United States Patent [19]

Holtman

[11] Patent Number: 4,678,464
[45] Date of Patent: * Jul. 7, 1987

[54] ABSORBENT STRUCTURE WITH RESERVOIRS AND A CHANNEL

[75] Inventor: Dennis C. Holtman, Flemington, N.J.

[73] Assignee: Personal Products Company, Milltown, N.J.

[*] Notice: The portion of the term of this patent subsequent to Feb. 26, 2002 has been disclaimed.

[21] Appl. No.: 704,671

[22] Filed: Feb. 22, 1985

Related U.S. Application Data

[63] Continuation-in-part of Ser. No. 489,980, Apr. 29, 1983, abandoned, which is a continuation-in-part of Ser. No. 474,396, Mar. 11, 1983, Pat. No. 4,501,586, which is a continuation-in-part of Ser. No. 207,524, Nov. 17, 1980, abandoned.

[51] Int. Cl.$^4$ ............................................ A41B 13/02
[52] U.S. Cl. .............................. 604/385 R; 604/379; 604/380
[58] Field of Search ............ 604/379, 380, 385.1, 604/378

[56] References Cited

U.S. PATENT DOCUMENTS

| | | | |
|---|---|---|---|
| 2,690,749 | 10/1954 | Nelson | 604/398 |
| 3,065,751 | 11/1962 | Gobbo, Sr. et al. | 604/375 |
| 3,430,629 | 3/1969 | Murphy | 604/372 |
| 3,736,931 | 6/1973 | Glassman | 604/385 |
| 3,741,212 | 6/1973 | Schulte | 604/375 |
| 3,749,627 | 7/1973 | Jones, Sr. | 604/370 |
| 3,897,784 | 8/1975 | Fitzgerald | 604/374 |
| 4,285,342 | 8/1981 | Mesek | 604/375 |
| 4,333,462 | 6/1982 | Holtman et al. | 604/368 |
| 4,333,463 | 6/1982 | Holtman | 604/368 |

Primary Examiner—C. Fred Rosenbaum
Assistant Examiner—Sherri E. Vinyard

[57] ABSTRACT

An absorbent structure is provided which contains a loosely compacted cellulosic fibrous batt having two reservoirs and a connecting channel. The absorbent structure may be an infant diaper, an adult diaper, a sanitary napkin and incontinence pad or the like.

13 Claims, 10 Drawing Figures

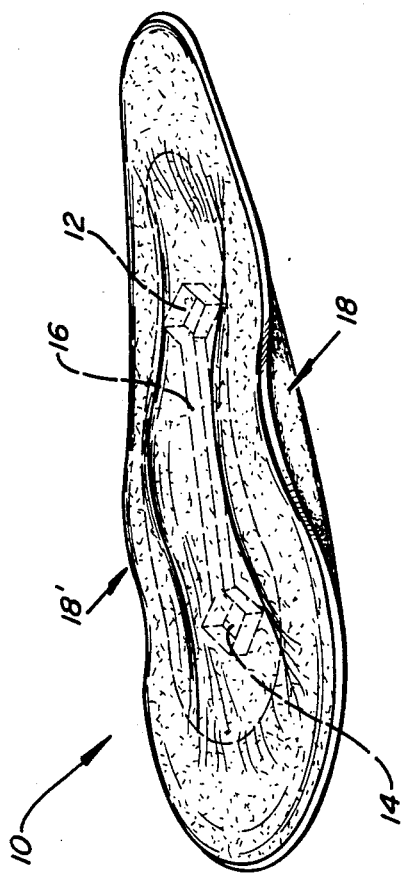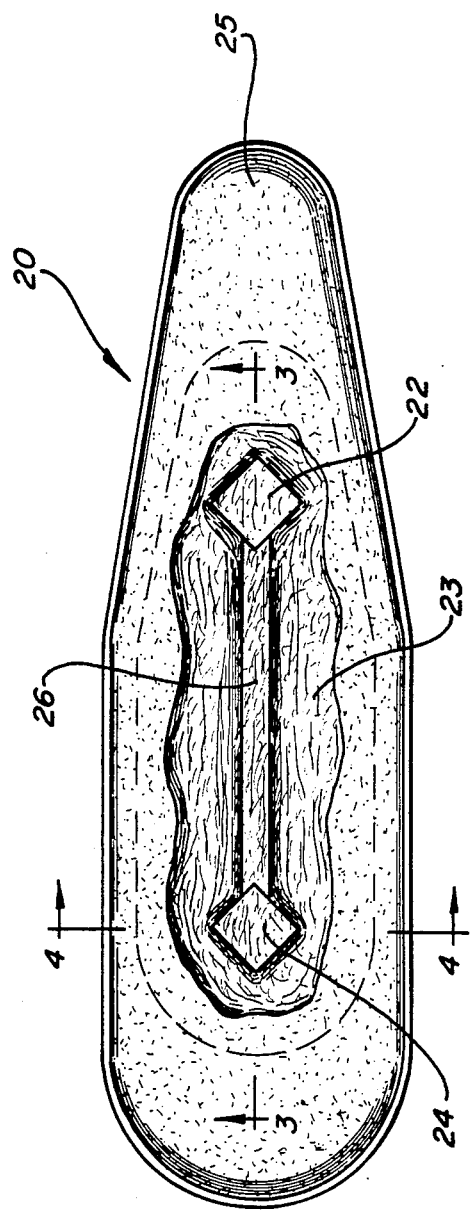

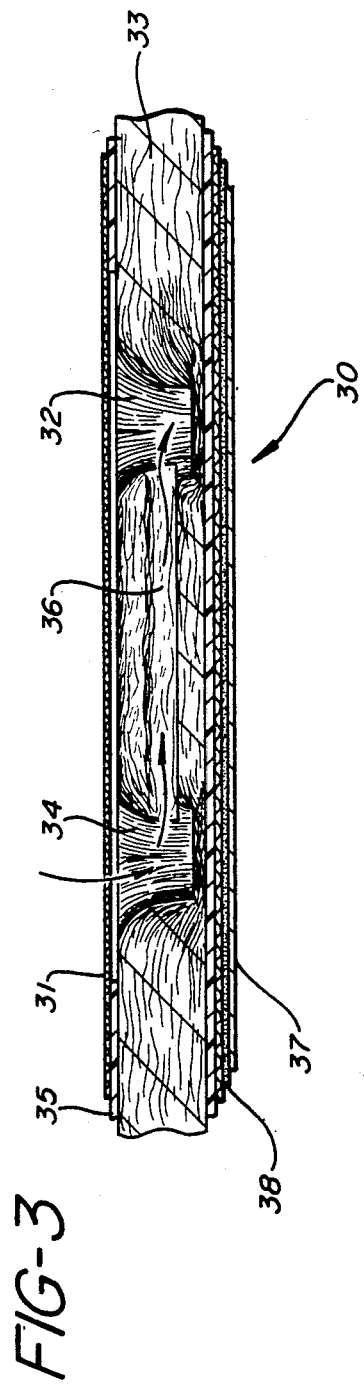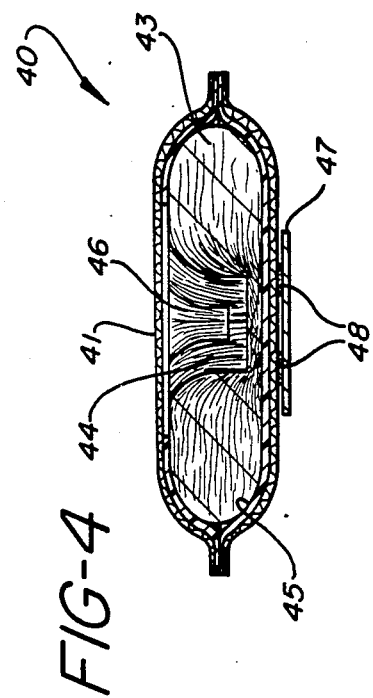

ABSORBENT STRUCTURE WITH RESERVOIRS AND A CHANNEL

This application is a continuation-in-part of copending application Ser. No. 489,980, filed Apr. 29, 1983, now abandoned which is a continuation-in-part of application Ser. No. 474,396, filed Mar. 11, 1983, now U.S. Pat. No. 4,501,586, which is continuation-in-part of application Ser. No. 207,524, filed Nov. 7, 1980, now abandoned.

BACKGROUND OF THE INVENTION

Disposable absorbent structures such as disposable diapers, sanitary napkins and incontinence pads have met with increased commercial acceptance in recent years primarily because of their convenience. Many different constructions have been proposed and used and some have met with widespread commercial success in spite of certain inadequacies in functional properties.

One of the most serious prior art problems has been the inability to provide a suitable construction that can accept a large void of body fluids. This is particularly true of the adult incontinent whether the incontinent be active and working or ill and bedridden. Various attempts have been made to provide special structures to absorb a large body fluid void. These include U.S. Pat. No. 3,441,024 to H. J. Ralph, U.S. Pat. No. 3,747,602 to H. J. Ralph, U.S. Pat. No. 3,968,798 to K. C. Hokanson, and U.S. Pat. No. 4,067,366 to R. L. Johnson. While these various constructions were designed to assist the adult incontinent, the problem of providing an overall disposable absorbent structure which will handle a full volume discharge of urine without leakage still remains.

Particularly when the incontinent is an adult, disposable structures generally have not accepted and held a full volume discharge of urine without leakage onto clothing. Although advances have been made in the sanitary napkin art to handle a full discharge of menstrual fluid (see U.S. Pat. No. 4,184,498 to P. Franco), disposable structures which will handle a complete urine void by an adult are absent. The present invention provides an absorbent structure which accepts and holds a complete urine void by an adult and which may be used as an infant diaper, an adult incontinence device, a sanitary napkin, an incontinence pad, or the like.

SUMMARY OF THE INVENTION

The present invention provides an absorbent structure to receive and contain body fluids comprising a loosely-compacted, cellulosic fibrous batt having a moisture-impermeable backing sheet on one side and a fabric cover which covers at least the side of the absorbent batt opposite the backing sheet on the other side. The cellulosic fibrous batt is substantially rectangular in shape whereby the length of the batt is at least about 1.5 times the width of the batt, the latter not exceeding about 5 inches. One surface of the batt contains two reservoirs spaced apart with a connecting channel. The reservoirs and the length of the channel are substantially centered on the longitudinal axis of the batt. The reservoirs and the channel are formed by compression of the cellulosic fibers. Each reservoir (1) has a capacity of at least about 10 cc, (2) covers at least one square inch of surface, (3) is situated between the center and one transverse end of the substantially rectangular cellulosic fibrous batt, (4) covers less than about twenty-five percent (25%) of the surface area of the batt, and (5) is formed by compression of the cellulosic fibrous batt so that the depth of the reservoir is more than one-batt half ($\frac{1}{2}$) the thickness of the batt. The depth of the channel need be only at least half the depth of the reservoirs. The width of the channel is generally from about $\frac{1}{4}$ to about $\frac{3}{4}$ the width of the reservoirs.

The two reservoirs and the channel act in concert to provide a three-dimensional product unlike the two dimensional products of the prior art. When the structure of the present invention is worn by the user the legs of the user apply pressure to the structure against each side, the structure selectively collapses at the channel more so than at the points of the reservoirs. This provides a boat shape by the back and front coming up (see FIG. 1) and the reservoirs staying open and available. The selective collapsing of the channel keeps the strike zone on the longitudinal centerline. By keeping the reservoirs on the longitudinal centerline, maximum use is made of each reservoir's capacity.

The absorbent structure may be incorporated in a disposable diaper such as for an infant or in an adult diaper with a larger liquid holding capacity. Furthermore, the absorbent structure may be incorporated in a sanitary napkin as well as in an incontinence pad. In each instance the opening of one reservoir or the channel is close enough to the void zone to allow immediate acceptance by the structure of the body fluid discharge. Generally, each reservoir will hold at least 75 percent of the body fluid discharged in one second.

The reservoirs and channel are created by compression of the loosely-compacted, cellulosic fibers. The compaction may be carried out by application of pressure in the shape desired for the reservoirs and channel. This may be done by a stamping-type operation or by an embossing roll or the like.

BRIEF DESCRIPTION OF THE DRAWINGS

FIG. 1 is a perspective view of one embodiment of the present invention;

FIG. 2 is a top view of the embodiment of FIG. 1 with a portion broken away for clarity;

FIG. 3 is a cross-sectional view taken along line 3—3 of FIG. 2;

FIG. 4 is a cross-sectional view taken along line 4—4 of FIG. 2;

DETAILED DESCRIPTION OF THE INVENTION

Figure 5:
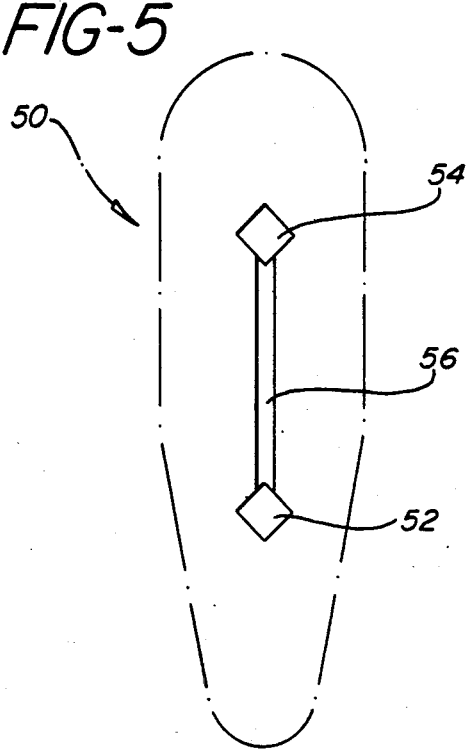
FIGS. 5, 6, 7 and 8 are top views of different embodiments of the present invention.
Figure 6:
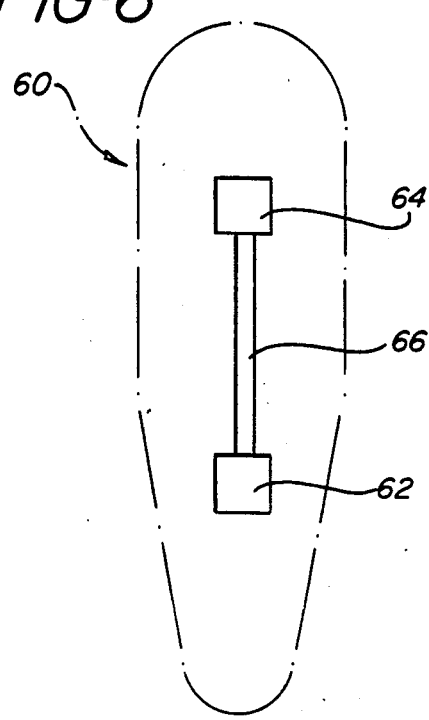
Figure 7:
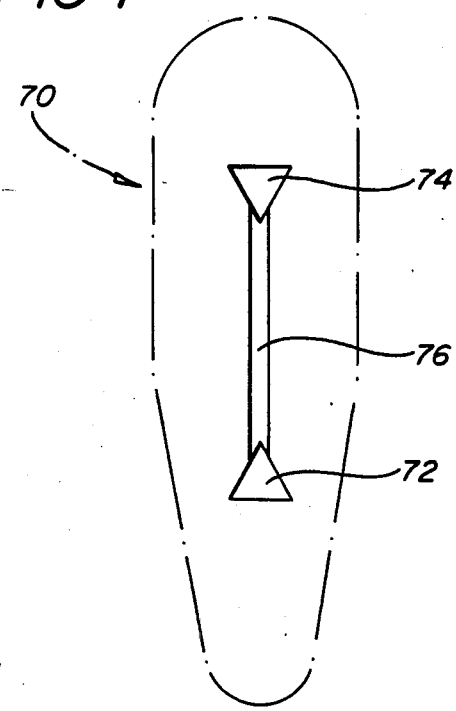
Figure 8:
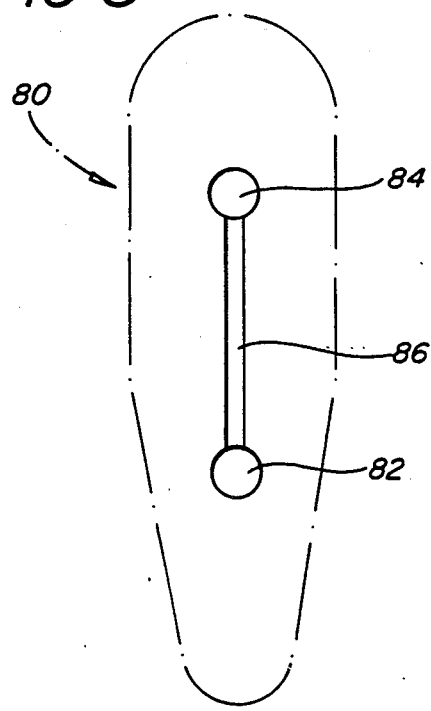

While this invention is susceptible of embodiment in many different forms, there is shown in the drawings, and herein will be described in detail, preferred embodiments of the invention and modifications thereof. It is understood that the present disclosure is to be considered as an exemplification of the principles of the invention and is not intended to limit the invention to the embodiments illustrated. The scope of the invention will be pointed out in the appended claims.

Referring to the drawings and particularly to FIG. 1, an absorbent structure 10 is provided with reservoirs 12 and 14 connected by a channel 16. The view in FIG. 1 is a perspective view of the absorbent structure as it would appear while being worn. Preferably, the underside of the structure has at least one adhesive strip whereby the structure can be fastened to the underwear of the wearer. The narrow portion of the pad is the back portion whereas the wider portion of the pad would be worn toward the front. The pad is satisfactory for use as a urinary pad or as a menstrual fluid pad. When the absorbent structure is being worn the thighs of the wearer would press at points 18 and 18' to cause the pad to form a boat-like shape where the sides of the pad are higher than the central portion. This assists in preventing leakage by any runover of fluid over the sides.

FIG. 2 is a top view of the pad of FIG. 1 showing an absorbent structure 20 having a back reservoir 22 and a front reservoir 24 connected by a channel 26. A portion of the opening is broken away to show the absorbent batt 23. A permeable facing 25 covers the upper surface. The sides and lower surface are protected by a moisture barrier such as a polyethylene backing.

FIG. 3 provides a cross-sectional view 30 of the absorbent structure of FIG. 2 along lines 3—3. The absorbent structure has reservoirs 32 and 34 connected by channel 36. If the pad were to be used as a urinary pad, it could be expected that the flow of the urine into the pad would follow the direction of the arrows. The absorbent structure has an absorbent batt of loosely-compacted cellulosic fibers 33 and is provided with a moisture barrier 35 which comes up around the sides and covers a portion of the top over which is placed a liquid permeable facing 31 which may be in the form of a nonwoven such as polyester or other suitable fabric. The under surface is provided with an adhesive strip 38 to which is attached a release liner 37. Upon removal of the liner the adhesive is available for fastening to the clothing of the wearer.

FIG. 4 is a cross-sectional view 40 of the absorbent structure of FIG. 2 along lines 4—4. This figure particularly illustrates the relationship of the depth of the channel in relation to the reservoirs. As can be seen, the reservoir 44 is deeper than the channel 46. This is a preferred embodiment, although the channel can be as deep as the reservoirs. The cellulosic batt 43 surrounded most of the way except for an opening on top by a moisture barrier 45. The facing 41 is used as an overwrap to wrap substantially all of the product. Release liner 47 is removed to provide the adhesive 48 for fastening to the clothing.

FIGS. 5, 6, 7 and 8 illustrate absorbent structures 50, 60, 70 and 80 respectively having different shapes for the reservoirs. These are merely illustrative and other shapes and size relationships may be used satisfactorily. In each case, the numeral ending in 2 and 4 denotes the reservoirs whereas the numeral ending in 6 depicts the channel.

Figure 9:
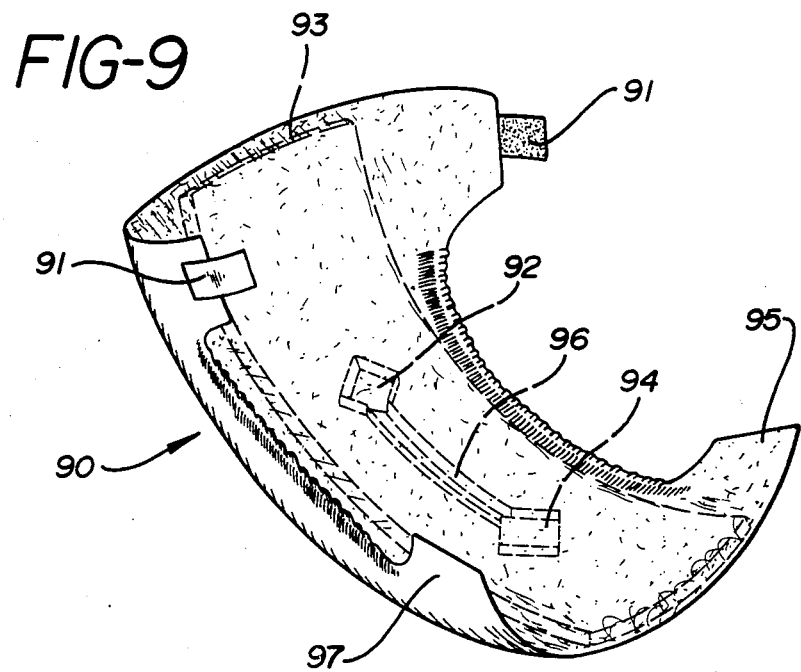
FIG. 9 is a perspective view of a diaper incorporating the absorbent structure of the present invention.
Figure 10:
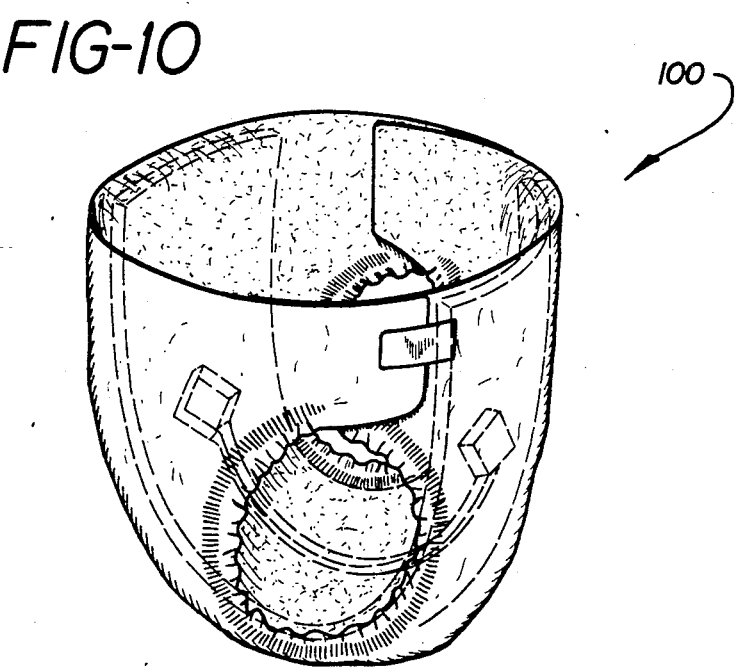
FIG. 10 is a perspective view of the diaper of FIG. 9 as it appears when worn.

The absorbent structure of the present invention may also be used in the form of a diaper. Such a diaper 90 is illustrated in FIG. 9. The cellulosic batt 93 is provided with reservoirs 92 and 94 with the connecting channel 96. Surrounding the cellulosic batt is a moisture-impermeable backing 97 and a moisture-permeable facing 95. The facing and backing are laminated in the margins and elastic is placed in the diaper for suitable fit. When the diaper is worn, tape tabs 91 secure the diaper about the wearer. In FIG. 10, the diaper 100 is illustrated as it would appear on a wearer.

The loosely-compacted cellulosic fibrous batt used in the absorbent structure of the present invention is formed from wood pulp fibers, rayon fibers, cotton linters or mixtures thereof. The batt is primarily held together by interfiber bonds requiring no added adhesive. In some instances the batt may contain synthetic fusible fibers such as polyethylene, polypropylene and the like. The batt is a coherent web of loosely-compacted cellulosic fibers preferably comminuted wood pulp fibers in the form of so-called "fluff". When the reservoirs and channels are created in the batt, a compressing or compaction process is used. The compression should be sufficient to create reservoirs of sufficient depth to hold at least 10 cc. The base of each of the reservoirs is a densified fibrous region wherein the fibers are compacted. The densified region quickly absorbs the body fluid and commences distribution of the fluid to other parts of the cellulosic batt particularly along the connecting channels. The channel is at least half the depth of the reservoirs. Although the base of the channel may not have as high a density as the base of a reservoir, there is at least some densifying of the fibers at the base of the channel. This densifying assists in transporting the liquid from one reservoir to another and to other parts of the cellulosic fibrous batt. The location and spacing of the reservoirs may be customized to optimize conditions for a particular use. In the instance of urinary pads, it is desirable for the reservoirs to be placed at least two inches apart but preferably not more than about six inches apart. It has been found that even in the use for a menstrual pad where the reservoirs may be relatively close together, that at least one-half inch between the reservoirs should be provided for the channel and preferably at least about an inch is suitable for the length of the channel. In all instances, the reservoirs and the channel should lie substantially on the longitudinal axis of the absorbent structure.

Although the absorbent structure is substantially rectangular, it can assume other shapes such as those illustrated in the drawings. One primary benefit afforded by the combination of the substantially rectangular shape of the batt, the reservoirs, and the connecting channel is that when the structure is worn, the thighs, whether they be those of an infant or an adult, place pressure on the sides and the sides come up in the central portion to provide a boat-like configuration. Such a configuration is highly desirable to prevent leakage of body fluids at the side edges. The absorbent structure is provided with a moisture barrier backing on the side away from the one receiving fluids. This barrier may come up around the sides and cover most of the top surface. However, it is necessary that both of the reservoirs and the channel be exposed to the surface for reception of fluid. The top surface or the entire surface may be overwrapped in a fluid permeable material such as a nonwoven fabric. For example, the fabric may be polyester, polyethylene, polypropylene, nylon, rayon or the like. Preferably, the fabric used for the cover is a lightweight fabric in the range of 0.3 to 5 ounces per square yard and with a density less than 0.2 grams per cc. The most suitable fabrics have unusually high elongation, loft, softness and drape characteristics. Though the cover is moisture-permeable, it is preferably of the type which after permeation of the moisture prevents strike back of the body fluid when the absorbent structure is approaching saturation.

The body of the cellulosic fibrous batt is substantially more wettable than the cover and tends to draw liquid away from the facing layer. Thus the void occurs and the cover is permeated and the liquid deposited in at least one reservoir. The individual fibers of the batt are extremely wettable and thus draw the liquid into the batt and along the channel to the other reservoir. The base of the reservoir is a densified fibrous region wherein the capillary radius is quite small. Thus, the capillary pressure is increased and the liquid is rapidly distributed to portions of the cellulosic batt. Furthermore, the base of the channel is of a higher density than the immediately surrounding areas except for the reservoir. Thus, this densified fibrous region at the base of the channel provides sufficient capillary pressure to transport the liquid to the other reservoir whereupon the highly densified base of the other reservoir further absorbs the liquid and distributes it. These densified fibrous regions at the base of the reservoirs and the channel provide the maximum capillary pressure because it combines the very low contact angle of the fibers of the batt with the high density of the densified fibers.

The individual fibers of the batt are extremely wettable, generally having liquid-fiber contact angles below about 30° in the optimum embodiment. The wickability or preferential absorptivity of the body of the batt for water is limited, however, by its low density which results in large effective capillary radius for the capillaries between adjacent fibers.

The pressure causing a liquid to enter a cylindrical capillary is expressed by the equation $$P = \frac{2\gamma \cos \theta}{r}$$

wherein
P is the capillary pressure,
$\gamma$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and increases with narrower capillary radii so that narrower capillaries will draw liquid from wider ones.

The relative wickability between the cover layer and the body of the fibrous batt is affected by both the relative densities of the layers and the relative wettability of the individual fibers in each layer. The individual fibers of the batt have substantially smaller liquid-fiber contact angles than those of the cover layer overcoming the density difference and providing a substantial overall increase in capillary pressure to absorb liquid into the body of the batt.

A densified fiber layer such as that at the base of the reservoirs and the channel provide the maximum capillary pressure because it combines the very low contact angle of the fibers of the batt with the high density (small capillary radius) of the densified fibers.

Thus, when urine is voided into an area in the cover layer, it partially wets a small portion of the cover layer and is passed through the cover layer, almost instantaneously, to the reservoir. It then comes into contact with the body of the batt surrounding the reservoir and the channel and is preferentially absorbed into the body of the batt because of the enhanced wettability of the reservoir and channel and particularly the base of the reservoir and channel. The same is true when the body fluid is a menstrual fluid or other liquid exudate.

In addition, it may be desirable to provide a paper-like densified layer on the side of the batt opposite the reservoir. The paper-like densified layer is formed by a slight moistening of the surface of the batt followed by light compaction using the application of pressure. U.S. Pat. No. 3,017,304 to Burgeni provides such a densified layer in a loosely-compacted cellulosic fibrous batt. This paper-like densified layer promotes wicking of liquid to all portions of the structure.

It will be understood by those skilled in the art that variations and modifications of the specific embodiments described above may be employed without departing from the spirit and scope of the invention as defined in the appended claims.

What is claimed is:

1. An absorbent structure comprising a loosely-compacted cellulosic fibrous batt substantially rectangular in shape and having a length at least about 1.5 times the width of the batt, the width not exceeding about 5 inches, one surface of said batt containing at least 2 reservoirs spaced apart with a connecting channel, said reservoirs and the length of the channel being centered on the longitudinal axis of the batt, each reservoir (1) has a capacity of at least about 10 cc, (2) covers at least one square inch of surface, (3) is situated between the center and one transverse end of the substantially rectangular cellulosic fibrous batt, (4) covers less than about twenty-five percent (25%) of the surface area of the batt, and (5) is formed by compression of the cellulosic fibrous batt so that the depth of the reservoir is more than one-half (½) the thickness of the batt, the channel depth being at least one-half the depth of the reservoirs; a moisture-permeable facing covering the surface of the batt containing the reservoirs; and a moisture-impermeable backing covering at least the surface opposite the surface containing the reservoirs.

2. The absorbent structure of claim 1 wherein the base of the reservoirs is a densified region of the fibers of the fibrous batt.

3. The absorbent structure of claim 1 wherein the surface of the absorbent batt opposite the surface containing the reservoirs is provided with a paper-like densified skin.

4. The absorbent structure of claim 1 wherein the backing is provided with an adhesive strip for securement of the structure when worn.

5. The absorbent structure of claim 1 in the form of a sanitary napkin.

6. The absorbent structure of claim 1 in the form of a disposable diaper.

7. The absorbent structure of claim 1 in the form of an incontinence pad.

8. An adult incontinence structure substantially rectangular in shape comprising a moisture-impermeable backing sheet; an absorbent loosely-compacted cellulosic fibrous batt superimposed on said backing sheet, and a moisture-permeable facing cover, covering at least the side of said absorbent batt opposite said backing sheet; said absorbent batt being provided with at least two reservoirs spaced apart with a connecting channel; said reservoirs and the length of the channel being centered on the longitudinal axis of the batt; each reservoir (1) has a capacity of at least about 10 cc, (2) covers at least one square inch of surface, (3) is situated between the center and one transverse end of the substantially rectangular cellulosic fibrous batt, (4) covers less than about twenty-five percent (25%) of the surface area of the batt, and (5) is formed by compression of the cellulosic fibrous batt so that the depth of the reservoir is more than one-half (½) the thickness of the batt, the channel depth being at least one-half the depth of the reservoirs.

9. The adult incontinence structure of claim 8 wherein the backing sheet is provided with an adhesive layer which functions as an adhesive strip for securement of the pad when worn.

10. A disposable diaper comprising a moisture-impermeable backing sheet; an absorbent loosely-compacted cellulosic fibrous batt superimposed on said backing sheet and a moisture-permeable facing superimposed on the side of the fibrous batt opposite said backing sheet; said absorbent batt being provided with at least two reservoirs spaced apart with a connecting channel; said reservoirs and the length of the channel being centered on the longitudinal axis of the batt; each reservoir (1) has a capacity of at least about 10 cc, (2) covers at least one square inch of surface, (3) is situated between the center and one transverse end of the substantially rectangular cellulosic fibrous batt, (4) covers less than about twenty-five percent (25%) of the surface area of the batt, and (5) is formed by compression of the cellulosic fibrous batt so that the depth of the reservoir is more than one-half (½) the thickness of the batt, the channel depth being at least one-half the depth of the reservoirs.

11. A sanitary napkin comprising a moisture-permeable outer layer containing an absorbent loosely-compacted cellulosic fibrous batt; said absorbent batt being provided with one surface of said batt containing at least two reservoirs spaced apart with a connecting channel; said reservoirs and the length of the channel being centered on the longitudinal axis of the batt; each reservoir (1) has a capacity of at least about 10 cc, (2) covers at least one square inch of surface, (3) is situated between the center and one transverse end of the substantially rectangular cellulosic fibrous batt, (4) covers less than about twenty-five percent (25%) of the surface area of the batt, and (5) is formed by compression of the cellulosic fibrous batt so that the depth of the reservoir is more than one-half (½) the thickness of the batt, the channel depth being at least one-half the depth of the reservoirs.

12. The sanitary napkin of claim 11 wherein the side opposite the reservoirs is provided with an adhesive layer which functions as an adhesive strip for securement of the napkin when worn.

13. The sanitary napkin of claim 11 wherein the base of the reservoirs is a densified region of the fibers of the fibrous batt.

* * * * *